United States Patent [19]

Van Besauw et al.

[11] 4,420,553
[45] Dec. 13, 1983

[54] PHOTOSENSITIVE RECORDING MATERIAL AND PHOTOGRAPHIC PROCESSES WHEREIN SAID MATERIAL IS USED

[75] Inventors: Jan F. Van Besauw, Mortsel; Luc H. Leenders, Tielen; Dirk M. D'hont, Mortsel; Hendrik E. Kokelenberg, Merksem; Rafaël P. Samijn, Wilrijk, all of Belgium

[73] Assignee: AGFA-GEVAERT N.V., Mortsel, Belgium

[21] Appl. No.: 376,596

[22] Filed: May 10, 1982

[30] Foreign Application Priority Data

May 15, 1981 [GB] United Kingdom ................ 8114926

[51] Int. Cl.$^3$ .......................... G03C 1/52; G03C 1/68
[52] U.S. Cl. .................................... 430/275; 430/281; 430/343; 430/285; 430/286; 430/287; 430/288; 430/916; 430/920; 430/495; 430/955; 204/159.23

[58] Field of Search ............... 430/281, 285, 286, 287, 430/288, 916, 275, 920, 495, 343, 955; 204/159.23

[56] References Cited

U.S. PATENT DOCUMENTS 4,252,887  2/1981  Dessauer ............................ 430/920

Primary Examiner—Won H. Louie, Jr.
Attorney, Agent, or Firm—William J. Daniel

[57] ABSTRACT

Photographic material comprising a supported or self-supporting binder layer incorporating a photoradical precursor compound in operative relationship with an image-forming precursor compound which is capable of taking part in image formation by reaction with the photoradicals formed by photoexposing said photoradical precursor, wherein the image-forming compound is a reducing compound containing Zerewitinoff active hydrogen for forming a print-out image or an ethylenically unsaturated compound capable of free-radical addition polymerization, and the photoradical precursor compound is a di- or tri(2,3-aryl substituted indolyl) compound free of Zerewitinoff active hydrogen.

7 Claims, No Drawings

PHOTOSENSITIVE RECORDING MATERIAL AND PHOTOGRAPHIC PROCESSES WHEREIN SAID MATERIAL IS USED

The present invention relates to a photosensitive recording material and photographic processes using the same.

More particularly, the present invention relates to a photosensitive recording material containing an organic photoradical-precursor compound.

The use of free radicals in image formation is known for the production of dye images and polymerization images, e.g. in the manufacture of photoresists and printing plates.

A broad survey of photoradical-precursor compounds and their use in photographic imaging is given by K. I. Jacobson and R. E. Jacobson in the book Imaging Systems, Mechanisms and Applications of Established and New Photosensitive Processes, The Focal Press London and New York (1976).

There is a constant search for photoradical-precursor compounds to produce effective image-forming compositions with dye precursor compounds and/or polymerizable substances.

Unlike ordinary chemical reagents, most free radicals cannot be stored as such but have to be formed as a result of the input of energy to a free-radical precursor compound. In a photographic process operating with photosensitive compounds producing free radicals, it is important to provide such compounds which remain stable under storage conditions in the dark and can be activated with a minimum of photon energy. A very useful class of free-radical precursor compounds consists of hexaarylbiimidazole compounds of which the 2,4,5-triarylimidazolyl radicals are useful oxidizing agents for leuco dyes as described, e.g., in G.B. Pat. No. 1,047,569 and U.S. Pat. No. 3,445,234 and are useful polymerization-initiating compounds for addition polymerization of $\alpha,\beta$-ethylenically unsaturated compounds as described, e.g., in U.S. Pat. No. 3,718,473.

We have found experimentally that the unsubstituted hexaarylbiimidazole compounds have a low stability and tend to prematurally set free imidazolyl radicals acting as oxidant which makes them less suited for application in a photographic material.

Other hexaarylbiimidazole compounds such as bis(2-o-chlorophenyl-4,5-diphenylimidazolyl) are much more stable but have absorption peaks which do not match always with the emission peak(s) of a lot of commercially available ultraviolet radiation sources so that there is a constant search for other photoradical precursors showing a better spectral matching with the emission spectrum of a particular radiation source.

According to the present invention a photosensitive recording material is provided incorporating a photoradical precursor with high storage stability in the dark and a high sensitivity to ultraviolet radiation of commercially available ultraviolet radiation sources.

The photosensitive recording material of the present invention comprises a supported or self-supporting binder layer incorporating an organic photoradical precursor compound in operative relationship with an image-forming precursor compound which is capable of taking part in image formation by reaction with the photoradicals formed by photoexposing the photoradical precursor compound, characterized in that the photoradical precursor compound is a di- or tri(2,3-aromatically substituted indolyl) compound free from Zerewitinoff active hydrogen, i.e. hydrogen, which is reactive with respect to methylmagnesium iodide.

The determination of Zerewitinoff active hydrogen is described, e.g., by I. L. Finar in Organic Chemistry, Vol. 1, Longmans, Green and Co Ltd, London (1963) p.350.

By "operative relationship" is meant in the present invention that the photoradicals produced by irradiating the photoradical precursor compound are in chemically reactive contact with the image-forming precursor compound.

The dimer compounds used according to the present invention can be represented by the following general formula:

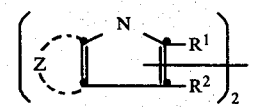

wherein:
Z represents the atoms necessary to close an adjacent carbocyclic aromatic ring including such ring in substituted form,
each of $R^1$ and $R^2$ is an aromatic substituent including a substituted aromatic substituent, the positions of the double bonds in the indole rings being determined by the position of the linkage between the rings, said compounds being free from Zerewitinoff active hydrogen.

The trimeric compounds for use according to the present invention are within the scope of the following general formula:

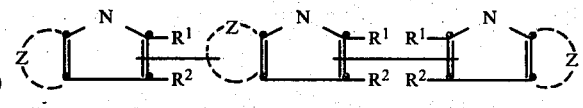

wherein:
Z, $R^1$ and $R^2$ have the meaning as defined above, the positions of the double bonds in the indole rings being determined by the position of the linkage between the rings, said compounds being free from Zerewitinoff active hydrogen.

The aromatic $R^1$ and $R^2$ substituents are carbocyclic or heterocyclic, preference being given to aromatic groups such as phenyl, biphenyl, naphthyl, furyl or thienyl. Substituents for these groups, if any, are free from Zerewitinoff active hydrogen and thus may be cyano, alkyl, haloalkyl, cyanoalkyl, aryl, alkoxy, aryloxy, alkylthio, arylthio, alkylsulphonyl, arylsulphonyl, nitro and halogen, e.g. chlorine.

The above dimer or trimer compounds can be prepared by oxidation with potassium permanganate of the corresponding diarylindole as described by Vinod Dave, Can.J. Chemisty, 50, (1972) p.3397-3401, which method yields a mixture of dimers and trimers including compounds with and without Zerewitinoff active hydrogen.

In a preferred preparation method the oxidation of 2,3-aromatically substituted indole is carried out in alkaline medium by means of a cyanoferrate(III) e.g. potassium cyanoferrate(III), which is used likewise for the preparation of hexaarylbiimidazole compounds starting from triarylimidazole ref. D. M. White & Sonnenberg, J.Am.Chem.Soc. 88 (1966) 3825-9. Both preparation methods, the last and the former mentioned being called preparation A and preparation B respectively, are illustrated hereinafter with 2,3-diphenylindole as starting compound. In preparation method A a mixture of dimer and trimer is produced with both being free of Zerewitinoff active hydrogen. 2,3-Diphenylindole itself can be prepared according to the method described by R. C. G. Fennell and S. G. P. Plant, J.Chem.Soc. (1932) p.2872.

PREPARATION A (UNDER YELLOW SAFE LIGHT)

Dimer A

To 53.8 g (0.2 mole) of 2,3-diphenylindole, dissolved in 600 ml of ethanol, a solution of 24 g (0.6 mole) of sodium hydroxide and 131.7 g (0.4 mole) of potassium hexacyanoferrate(III) in 400 ml of water was added at once at room temperature. A precipitate formed immediately.

The mixture was stirred for 4 h. The precipitate was collected on a suction funnel, washed with water and dried at room temperature. Yield: 30 g of crude product. It was purified by column chromatography on silica gel of 60 um average particle size with a mixture of methylene chloride and ethyl acetate (95 to 5 parts by volume) as eluent.

The dimer A fraction was identified by comparison with an authentic sample obtained by preparative thin-layer chromatography (TLC) on silicagel (60 μm) and with the use of methylene chloride with varying quantities of methanol as eluent. Yield: 7.1 g (13% by weight) of dimer A (white substance), melting point: 203° C. By infra-red (IR) spectroscopy, mass spectrometry and by $^{13}$C nuclear magnetic resonance (NMR) dimer A has been proved to be within the scope of the following formula:

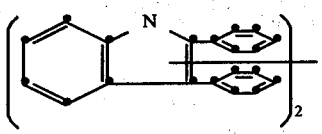

Instead of purifying the above crude product by column chromatography the crude product (53 g) was stirred in 650 ml of boiling ethanol and filtered while hot. The residue was purified by washing twice with diethyl ether (500 and 150 ml respectively). After drying, the product obtained by said washing technique weighed 13 g (yield 24%) and was used as such in Example 16 proving that its photochemical activity was not substantially lower than after purification by column chromatography.

Trimer A

By said column chromatography from the crude product also a fraction 5.5 g (yield: 10% by weight) of a light brown solid (melting point 210°-216° C.) with lowest Rf was separated.

According to IR spectroscopy, mass spectrometry and $^{13}$C-NMR data could be concluded that the structure is trimeric.

The trimeric compound is within the scope of the following formula:

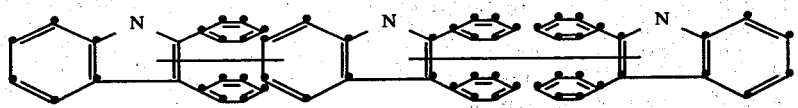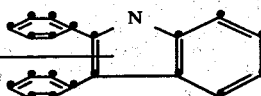

PREPARATION B (UNDER YELLOW SAFELIGHT)

Dimer B 53.8 g (0.2 mole) of 2,3-diphenylindole were dissolved in 140 ml of acetone. While stirring, 10.7 g (0.068 mole) of potassium permanganate were added in portions of about 0.5 g within a period of 45 min.

The reaction was exothermic and the temperature rose from 20° to 35° C. The mixture was stirred for another hour and then filtered. The filtrate was concentrated at reduced pressure and yielded 30 g of solid crude product.

From the crude product dimer B was isolated by column chromatography by using the method described for dimer A in preparation A.

Dimer B was separated as a cream-white solid. Yield: 9 g (17% by weight), melting point: 246°-248° C.

According to IR-spectroscopy and $^{13}$C NMR data the structure of dimer B was found to correspond to:

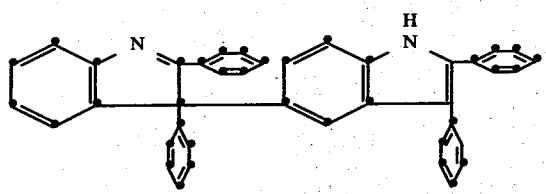

wherein in the NH group a Zerewitinoff active hydrogen is present, which lowers the activity of said dimer for the purpose of the present invention, said dimer B being therefore excluded therefrom.

The 2,3-aromatically substituted indolyl radical formed in the photo-exposure can be represented by the following formula:

wherein the dotted circle in the pyrrole ring stands for 5 delocalized electrons which satisfy the valences of the carbon and nitrogen atoms of the indolyl ring, 4 of said electrons being paired (which may be represented as two conjugated double bonds), the fifth electron being odd, and Z, $R^1$ and $R^2$ have the same meaning as described above.

The formation of radicals from dimer A has been observed by electron spin resonance (ESR) spectrometry.

The apparatus used was a VARIAN E4 (registered trade mark) ESR-spectrometer. The radicals were generated by irradiating a methylene chloride solution of dimer A with ultraviolet light having a wavelength of 316 nm.

A general description of the ESR-technique is given by F. Bär et al., Chemie in unserer Zeit 9 (1975) p.18–24 and 43–49.

In a first group of photosensitive recording materials according to the present invention a di- or tri(2,3-aromatically substituted indolyl) compound being free from Zerewitinoff active hydrogen is present in a binder layer on a support in operative relationship with a reducing compound containing Zerewitinoff active hydrogen such as in:

(I) an aromatic polyhydroxyl compound or an oxidizable derivative thereof, e.g. aromatic polyhydroxyl compounds wherein one of the hydroxyl groups has been replaced by an alkoxy group, (II) an aromatic polyamino compound or an oxidizable derivative thereof, e.g. N-alkyl-substituted derivatives, (III) an aromatic hydroxyl-amino compound i.e. an aromatic compound containing a hydroxyl and an amino group or an oxidizable derivative thereof, or (IV) a compound according to the following general formula:

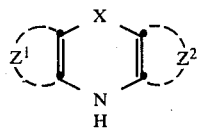

wherein:

X represents oxygen, sulphur, —NH—, —CH$_2$—, —CH=CH—, or

and each of Z$^1$ and Z$^2$ represents the necessary atoms to close a carbocyclic aromatic ring or substituted carbocyclic aromatic ring, e.g. a benzene ring or a substituted benzene ring.

Reducing compounds of class (I) are, e.g.:

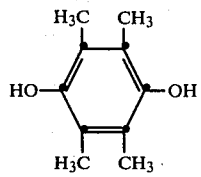
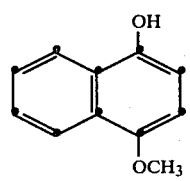
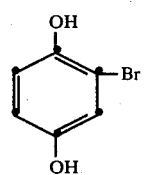
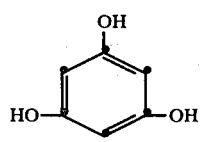
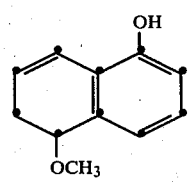

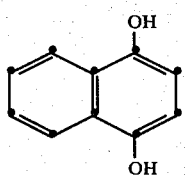
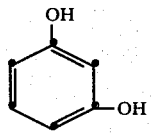
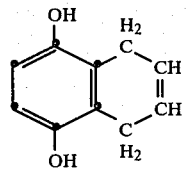
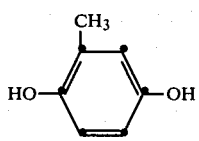
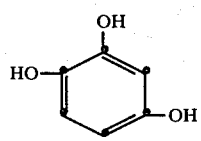
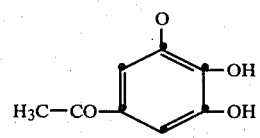
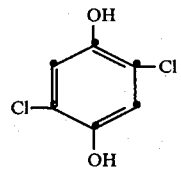
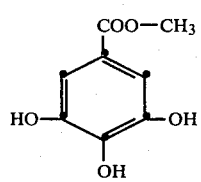

Reducing compounds of class (II) are e.g.:

Reducing compounds of class (III) are e.g.:

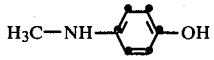
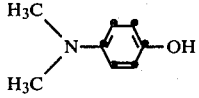
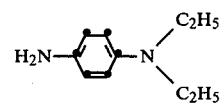
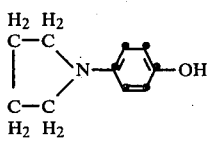
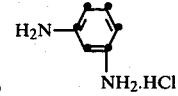
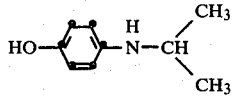
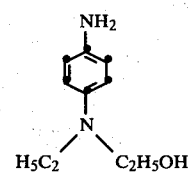
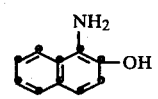

-continued

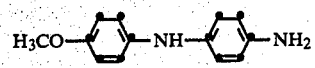

Reducing compounds of class (IV) are, e.g.:
(a) amino-9,10-dihydroacridines
(b) aminodihydrophenazines
(c) aminophenothiazines
(d) aminophenoxazines.

Of these compounds (a), (b), (c) and (d) examples are given in the U.S. Pat. No. 3,734,733.

For application in a photographic process including the production of an image through the image-wise transfer by heat of a reducing compound to an image-receiving material said oxidizable components are preferably volatilizable, e.g. between a temperature of 60° to 140° C., such as 4-methoxy-α-naphthol.

Said process comprises the steps of (1) image-wise exposing to ultraviolet radiation a photosensitive recording element comprising a photo-oxidizing di- or tri(2,3-aromatically substituted indolyl) compound free from Zerewitinoff active hydrogen in chemically reactive contact with an organic reducing compound containing Zerewitinoff active hydrogen whose reducing properties are destroyed by reaction with the photoradicals of said indolyl compound, (2) uniformly contacting the thus exposed element with a layer of an image-receiving material containing a substance active in image-formation on heating by reaction with said reducing compound to produce a distinctive colouration, and (3) heating the exposed element while in contact with said image-receiving layer to produce therein a visible image corresponding to the unexposed areas of said element by reaction of the transferred reducing compound in said areas with said substance.

Suitable substances active in image formation in a receiving material by reaction with unoxidized reducing compounds for forming a coloured product are described, e.g., in said U.S. Pat. No. 3,734,733 and belong to the following groups (V), (VI), and (VII):

(V) heavy-metal compounds, e.g. silver compounds, (VI) colour couplers with which the image-wise transferred reducing compounds can react by oxidative coupling to form a dye, (VII) diazonium salts for coupling with phenols or naphthols that contain, e.g., an amino group, so that coloured compounds are formed of the type known from diazotype recording.

Within the scope of said first group of photosensitive materials are likewise print-out materials wherein the reducing compound yields directly in said material itself a coloured product by image-wise exposure, the print-out image formation proceeding by oxidation of the reducing compound or by an oxidative coupling reaction using the photoradicals of said photodissociable di- or triindolyl compound as the oxidizing substance. Selected reducing compounds for that purpose are described under the heading "(B) oxidizable component" in the U.S. Pat. No. 3,585,038 and have a formal oxidation potential of 1.35 volts or less relative to a standard calomel electrode, and are selected from the class consisting of:

(1) p-arylene-di-t-amines wherein the arylene groups are phenylene or diphenylene and the groups attached to the amine nitrogen are $C_1$–$C_4$ alkyl or $C_1$–$C_4$ alkylene;

(2) p-phenylenediamines wherein one amino group is primary and the other is tertiary in which the groups attached to the tertiary nitrogen are $C_1$–$C_4$ alkyl, said p-phenylenediamines being in admixture with a coupling compound selected from phenols, N,N-di($C_1$–$C_4$-alkyl) phenylamines and active methylene coupling compounds;

(3) iminohydrazides and their N-acyl derivatives which are oxidizable to diazonium compounds, in admixture with a coupling compound selected from phenols, N,N-disubstituted arylamines and active methylene coupling compounds;

(4) o,o'-disubstituted phenols wherein the substituents are halogen, $C_1$–$C_4$ alkyl or $C_1$–$C_4$ alkoxy, and (5) organic sulphydryl compounds.

Other suitable dye-forming oxidizable components for print-out imaging are dyes in leuco form as described, e.g., in G.B. Pat. No. 1,047,569, more particularly belonging to the group consisting of:

a. aminotriarylmethanes including
  (i) carbocyclic aromatic groups and
  (ii) heterocyclic aromatic groups
b. aminoxanthenes
c. aminothioxanthenes
d. amino-9,10-dihydroacridines
e. aminophenoxazines
f. aminophenothiazines
h. aminodiphenylmethanes
i. leucoindamines
j. aminohydrocinnamic acids, their esters, amides and cyanoethanes
k. hydrazines
l. leuco indogoid dyes
m. amino-2,3-dihydroanthraquinones
n. tetrahalo-p,p'-biphenols
o. 2-(p-hydroxyphenyl)-4,5-diphenylimidazole
p. phenethylanilines.

In a photographic material known as DYLUX (registered trade mark of du Pont de Nemours, USA) colour formation occurs as described in G.B. Pat. No. 1,057,785 through oxidizing free radicals produced from the already mentioned photo-oxidant, i.e. a 2,4,5-triarylimidazolyl dimer, by reaction with an organic colour generator, e.g. a dye in leuco form as defined above. The photographic material includes also a redox couple comprising a reductant component and an oxidant component capable of undergoing a photoinitiated redox reaction when irradiated with actinic radiation of a wavelength different from that causing the photo-oxidant to oxidise the organic colour generator, the photoinitiated redox reaction between the two components of the redox couple forming a reducing agent which reacts with and deactivates the photo-oxidant.

The present invention includes such photosensitive recording materials wherein the formation of a visible image through photo-oxidation of an oxidizable component, i.e. a leuco dye can proceed with ultraviolet radiation (W1) photolytically forming free radicals from a di- and/or tri(2,3-aromatically substituted indolyl) compound free from Zerewitinoff active hydrogen and wherein said material also contains a redox couple capable of producing by exposure to visible light (W2) reductant scavenging indolyl radicals formed in a subsequent ultraviolet radiation exposure of the material to form colourless products.

A preferred photosensitive recording material capable of undergoing photo-stabilization contains the following components:

(A) an acid salt of a substantially colourless oxidizable substituted amino-triarylmethane leuco dye which is not oxidized by atmospheric oxygen under storage conditions at room temperature, (B) a bi and/or tri(2,3-aromatically substituted indolyl) compound whose photoradicals formed by irradiation of the indolyl compound in the spectral range of 250 to 370 μm will oxidize compound (A) to form a dye, (C) a redox couple which consists of (1) pyrenequinone or phenanthrene quinone as oxidizing agent and (2) a compound corresponding to one of the following general formulae: $N[(CH_2)_nCOOR^5]_3$ or $N[(CH_2)_n-OCOR^5]_3$, wherein n is 1 or 2 and $R^5$ is a $C_1-C_4$ alkyl group, e.g. the $C_1-C_4$ alkyl ester of nitrilotriacetic acid or trimethyl-3,3′,3″-nitrilotripropionate.

In print-out image forming photosensitive recording materials of the present invention the di- and/or tri(2,3-aromatically substituted indolyl) compound(s) preferably is (are) present in an amount sufficient to yield a visible image with an optical density of at least 0.8.

In a second group of photosensitive recording materials according to the present invention a di- or tri(2,3-aromatically substituted indolyl) compound free from Zerewitinoff active hydrogen is present in a photopolymerizable layer in a binder on a support in operative relationship with (1) at least one non-gaseous ethylenically unsaturated compound capable of free-radical initiated, chain-propagating addition polymerization, and (2) a free radical producing electron-donor agent from which an electron can be abstracted by a photolytically formed indolyl radical of said indolyl compound to yield a free radical which reacts with the unsaturated compound (1) to initiate the addition polymerization thereof.

Preferred agents (2) producing free radicals are organic amines. These include organic compounds of the type $R_3^{10}N$ wherein an $R^{10}$ may be H but at least one $R^{10}$ is an organic radical connected to the N through a $—CH_2R^{11}$, $—CHR_2^{11}$ or $—CR_3^{11}$ group where $R^{11}$ is hydroge, hydrocarbon or substituted hydrocarbon. Especially useful are tertiary amines where each $R^{10}$ is connected to N through a carbon atom which, in turn, is attached only to carbon or hydrogen. The most useful amines are aromatic amines where one of the $R^{10}$ groups is phenyl, tolyl, naphthyl, etc.

Another useful class of free radical-producing electron-donor agents (2) consists of mercaptans having the structure $R^{12}SH$ wherein $R^{12}$ is an alkyl, arylalkyl, aryl or heterocyclic group. Examples of representatives of these both classes of radical-producing electron-donor agents are described in U.S. Pat. No. 3,479,185. A preferred radical-producing electron-donor agent is 2-mercaptobenzoxazole.

The photopolymerizable layer including said compounds (1) and (2) in operative contact with a di- or tri(2,3-aromatically substituted indolyl) compound may be spectrally sensitized with p-aminophenyl ketones e.g. Michler's ketone, and with derivatives of aryl ketones and Michler's ketone, and with derivatives of aryl ketones and p-dialkylaminoarylaldehydes described in U.S. Pat. No. 4,162,132 for enhancing the sensitivity of photopolymerizable compositions including a hexaarylbiimidazolyl compound.

Particularly useful ethylenically unsaturated compounds capable of free-radical initiated, chain-propagating addition polymerization contain a plurality of ethylenically unsaturated bonds as e.g. in unsaturated esters of polyols. Very useful esters are, e.g., pentaerythritol triacrylate, polyethylene glycol diacrylate, triethylene glycol diacrylate, polyethylene glycol dimethacrylate, polymethylene diacrylate, trimethylolpropane triacrylate and pentaerythritol tetraacrylate.

Suitable binding agents are, e.g., polystyrene, polymethyl methacrylate, polyvinyl acetate, polyvinylbutyral, partially saponified cellulose acetate and other polymers that are soluble in the same solvents as used for the free radical producing substances. The ratio of polymerisable monomer to binding agent obviously influences the photopolymerisation. The larger this ratio, the higher the polymerisation rate generally will be for a particular polymerisable compound. As a result of the use of the above binding agents the final photopolymerizable coating is fairly hydrophobic.

The present invention includes a photographic process for the production of a relief image comprising the steps of image-wise exposing to ultraviolet radiation a photosensitive recording material comprising a support coated with a photopolymerizable layer as referred to hereinbefore, whereby in the exposed areas at least one ethylenically unsaturated compound is polymerised, and removing the non-exposed or insufficiently exposed portions of said layer by washing with a solvent for the binder.

According to an embodiment for wash-off processing the photosensitive photopolymerizable layer includes a homogeneous mixture of a hydrophilic colloid binder and at least one water-soluble ethylenically unsaturated compound, said mixture having uniformly distributed therethrough at least one of said di- or tri(2,3-aromatically substituted indolyl) compounds and at least one electron-donor agent producing free-radicals.

Monomeric compounds for use in the photopolymerizable layer of the last mentioned embodiment are, e.g., water-soluble, addition-polymerizable ethylenically unsaturated vinyl or vinylidene compounds described, e.g., in U.S. Pat. No. 3,236,644 and water-soluble acrylic monomers, more particularly acrylic acid, and water-soluble derivatives of acrylic acid, e.g. methacrylic acid, acrylamide, N,N-methylene bisacrylamide, metal acrylates, acrylonitrile, vinylpyrrolidinone, vinylpyridines and quaternary salts thereof. Of these monomers, the acrylamides and metal acrylates, e.g., calcium diacrylate, are particularly suitable for producing homogeneous mixtures with non-light-sensitive hydrophilic colloid binding agents such as e.g. gelatin, casein, zein, ethylcellulose, cellulose acetate phthalate, polyvinylpyrrolidinone and polyethylene glycols having a molecular weight between 4,000 and 20,000.

Suitable binder concentrations are in the range of 5 percent to about 60 percent by weight of the total weight of the photopolymerizable layer.

Suitable indolyl compound photo-initiator concentrations can be found by means of a series of tests with increasing amounts of photo-initiator(s), but amounts ranging from 0.005 percent to about 10 percent by weight with respect to the total weight of the photopolymerizable layer are normal.

The thickness of photopolymerizable layers suitable for wash-off processing may vary within wide limits, but is usually in the range of 0.5 to 25 μm.

In a special embodiment of the invention for wash-off processing the photopolymerizable layer comprises as binding agent an alkali-soluble polymer. By the use of such binding agents the photosensitive recording layer, after exposure to light, may be developed in aqueous alkaline medium so that the use of expensive and sometimes inflammable organic solvents for washing away the unexposed areas of the photosensitive layer is avoided.

Particularly useful alkali-soluble polymers are copolymers with units of unsaturated monocarboxylic acids, e.g. acrylic acid, methacrylic acid, and crotonic acid, unsaturated dicarboxylic acids, e.g. maleic acid, fumaric acid, itaconic acid, and citraconic acid as well as half-esters and half-amides of these dicarboxylic acids. These unsaturated carboxylic acids are copolymerised with ethylenically unsaturated compounds, which are substantially insoluble in alkaline medium and which are present in the copolymer in such a proportion that the copolymer itself remains soluble in alkaline medium. Ethylenically unsaturated compounds that can be used for the copolymerization are styrene and derivatives thereof, vinyl chloride, vinylidene chloride, vinyl esters such as vinyl acetate, acrylates, methacrylates, acrylonitrile, methacrylonitrile e.g. copoly(ethylene/maleic acid) and copoly(methyl methacrylate/methacrylic acid).

Especially suitable are the alkali-soluble copolymers of methyl methacrylate and methacrylic acid wherein the ratio by weight between the monomeric units is between 90:10 and 75:25, more preferably between 85:15 and 80:20, and wherein the intrinsic viscosity of the copolymers measured in tetrahydrofuran at 20° C. is between 0.05 and 0.20 dl/g, corresponding to molecular weights of about 7000 to 40,000.

These alkali-soluble copolymers of methyl-methacrylate and methacrylic acid combine easy removability of the non-exposed portion with good mechanical strength i.e. resistance to abrasion of the exposed portions.

A photosensitive recording material according to the present invention comprises according to a preferred embodiment a photopolymerisable ethylenically unsaturated (preferably plurally unsaturated) compound, examples of which have been given hereinbefore, a mixture of said di- and/or tri(2,3-aromatically substituted indolyl) compound and an electron-donor producing free radicals as defined hereinbefore, and an alkali-soluble copolymer of methyl methacrylate and methacrylic acid. The layer preferably has a thickness between 0.5 and 5 μm.

The amounts of binding agent and photopolymerisable compound in the photosensitive layer are preferably such that an exposure of said layer to ultraviolet radiation of maximum 1 minute at room temperature (20° C.) can effect a decrease in solubility of the exposed parts such that these parts do not dissolve in an aqueous solution (20° C.) of 0.5 to 3% by weight of sodium hydroxide within 20 seconds. Weight ratios of alkali-soluble polymer to photopolymerisable compound between 1:2 and 5:1 are preferred.

The amount of indolyl compound producing free radicals added to the mixture of alkali-soluble polymer and of polymerisable compound may vary between wide limits.

According to an embodiment a photosensitive recording material according to the present invention contains in the photopolymerisable layer water-insoluble monomers, e.g. the already mentioned esters of polyols, included in dispersed state in a hydrophilic colloid binder. In that embodiment the photosensitive recording material comprises a photopolymerisable layer including a hydrophilic binder having uniformly dispersed therethrough a phase containing (1) at least one water-insoluble ethylenically unsaturated monomer capable of forming a polymer by free radical-initiated chain-propagating addition polymerization, and (2) at least one free-radical producing composition activatable by ultraviolet radiation yielding free radical polymerization initiator(s), said composition containing a di- or tri(2,3-aromatically substituted indolyl) compound free from Zerewitinoff active hydrogen, and at least one free radical producing electron-donor agent wherefrom an electron can be abstracted by a photolytically formed indolyl radical of said dimerized or trimerized indolyl compound.

These photopolymerizable layers may be used for the production of a photoresist by a wash-off processing as described, e.g., in the U.S. Pat. No. 3,615,567 or for making metal images by etching through the obtained permeability pattern without applying wash-off removal of the unexposed portions of the photopolymerisable layer or for making printing plates, e.g., gravure printing plates as described, e.g., in the U.S. Pat. Nos. 3,718,473 and 3,879,204.

The size of the dispersed photopolymerizable droplets including said composition producing free radicals ranges e.g. from 0.1 to 10 μm. Dispersion is improved with the aid of a surfactant. Useful surfactants are, e.g., alkylnaphthalene sulphonic acid salts, organic esters of phosphoric acid, benzyl alcohol, octyl alcohol, lauryl alcohol, sodium lauryl sulphate, sulphonated derivatives of fatty acid amides and the condensation products of octyl phenyl and sorbitan monolaurate with polyoxyethylene oxide. Low-boiling solvents which are removed before coating of the dispersion are likewise suitable aids to incorporate the water-insoluble polymerizable monomers in a hydrophilic colloid binder. Examples of such solvents are ethyl formate, ethyl acetate, propyl acetate, n-butyl acetate, ethyl butyrate, hydrocarbons e.g. benzene, chlorinated hydrocarbons e.g. methylene chloride, and ethers e.g. diethyl ether.

The amount by weight of dispersed photopolymerizable material including the monomer(s) and photoinitiator(s) with respect to the hydrophilic binder may vary within a broad range but is preferably within the weight ratio range of 0.1/1 to 10/1.

The thickness of the layer containing the dispersed monomer(s) is, e.g., in the range of 0.1 μm to 25 μm.

The hydrophilic colloid binder for the dissolved or dispersed monomer is preferably gelatin but other natural and synthetic water-permeable organic colloid binding agents can be used. Such agents include water-permeable polyvinyl alcohol and its derivatives, e.g. partially hydrolyzed polyvinyl acetates, polyvinyl ethers, and acetals. Useful polyvinyl acetals include polyvinyl acetaldehyde acetal and polyvinyl butyraldehyde acetal. Further are to be mentioned hydrophilic cellulose ethers and esters, alginic acid and polyvinylpyrrolidone.

The present invention includes a recording method in which the photopolymerizable layer is used to form metal images. Said method includes the steps of:

(1) information-wise exposing to UV-radiation a recording material comprising a transparent film support bearing an opaque metal coating and thereon an alkali-soluble photopolymerizable layer as hereinbefore defined;

(2) overall contacting the photopolymerizable layer with an aqueous alkaline liquid to remove selectively the non-exposed or insufficiently exposed portions of that layer, and (3) contacting the uncovered portion of the opaque metal layer with a liquid that is capable of chemically removing (etching) said portions without removing the exposed portions of said layer.

The concentration of alkaline substance, e.g. potassium hydroxide, used for developing the resist layer, i.e. for selectively removing the unexposed photopolymerizable layer portions, may vary widely. Thus for example 0.4 to 7.5% by weight aqueous solutions of potassium hydroxide may be used.

Other alkaline substances which may be used for washing away the non-exposed portions of the photopolymerizable layer include 0.25 to 5% aqueous solutions of sodium hydroxide and 1 to 10% aqueous solutions of potassium carbonate.

For the production of line or screen images useful in the graphic art field said photopolymerizable layer is coated onto a substantially opaque, preferably relatively thin metal coating on a film support, the metal coating being etchable and thus serving as imaging layer. Particularly good results are obtained with tellurium and tellurium alloy coatings preferably having a thickness in the range 50 nm to 500 nm and bismuth coatings preferably having a thickness in the range 25 nm to 300 nm.

According to one embodiment in the composition of the metallic imaging layer tellurium alloys comprising at least 50 atomic percent of tellurium are used. Typical tellurium compositions, which are etchable with an aqueous hypochlorite solution, are described e.g. in the published German patent application (DE-OS) No. 2,723,613.

According to another and more preferred embodiment the imaging metal layer consists of bismuth. Bismuth possesses the advantage of directly adhering to organic resin supports such as a polyethylene terephthalate support when deposited thereon from bismuth vapour under reduced pressure conditions. Typical bismuth coatings have been described in DE-OS No. 2,723,613.

Vapour deposition techniques are sufficiently known to those skilled in the art e.g. of preparing photoconductive selenium coatings (see e.g. U.S. Pat. No. 3,874,917 of Charles Wood, John C. Schottmiller and Francis W. Ryan and U.S. Pat. No. 3,884,688 of John C. Schottmiller and Francis W. Ryan).

Bismuth forms a black, non-light-reflecting coating showing no crazing and it provides a very high spectral density. Indeed, a bismuth layer having a thickness as low as 80 nm shows a spectral density of about 3. A 100 nm bismuth layer has a spectral density of about 5.

A bismuth layer for a recording material according to the present invention is preferably applied to a polymeric film support, e.g. a sheet or belt. Preferably a polyethylene terephthalate support, e.g. of 0.07 to 0.1 mm thickness, is used.

The thickness of the dried photosensitive photopolymerisable recording layer may be between 0.5 and 20 $\mu$m, preferably between 1 and 5 $\mu$m.

For the chemical etching of a tellurium-containing layer preferably aqueous solutions of 0.5 to 30% of sodium hypochlorite are used.

For the etching of a bismuth layer preference is given to aqueous acidic iron(III) chloride solution. The concentration of iron(III) chloride is, e.g., in the range of 5 to 40% by weight. Said solution contains preferably from 0.25 to 1% by weight of citric acid.

A likewise useful etching solution for the removal of bismuth is an aqueous solution containing 3 to 6% by weight of hydrogen peroxide and 5 to 10% by weight of sulphuric acid. Instead of hydrogen peroxide sodium perborate $NaBO_2.H_2O_2.3H_2O$ or urea peroxide $NH_2CONH_2.H_2O_2$ can be used.

Photosensitive recording materials according to the present invention are prepared by coating the ingredients forming the photosensitive layer to the selected substrate according to a known coating technique, e.g. spin-coating, whirl-coating, spraying, dip-coating, roller-coating, air-knife coating, doctor-blade coating, etc. The coating composition may comprise besides the ingredients referred to hereinbefore matting agents, e.g. silica particles in association with urea-formaldehyde resin, e.g. of the type described in the published European patent application No. 0003627, polymethylmethacrylate particles, etc., antistatic agents, coating aids e.g. anionic and cationic surface-active agents, silicone oils, etc.

The photosensitive recording materials of the invention may be exposed to any source of ultraviolet radiation, more particularly radiation of wavelengths in the range 250–400 nm, preferably 300–400 nm. Suitable light sources include carbon arcs, mercury vapour lamps, fluorescent lamps, argon glow lamps, photographic flood lamps and tungsten lamps. Moreover, ordinary daylight may also be used. Pulsed xenon lamps and tungsten lamps emitting to a minor amount in the ultraviolet region and mainly in the visible light range may likewise be used since some of the sensitizers mentioned hereinbefore extend the spectral sensitivity into the visible light range.

The invention is further illustrated with some specific examples without limiting it thereto. All parts, percentages and ratios are by weight, unless otherwise indicated.

EXAMPLES 1-3

These examples demonstrate the degree of operability of the prepared dimers A and B and of trimer A in a dye-forming system.

Preparation of the photosensitive recording materials

An unsubbed polyethylene terephthalate support having a thickness of 100 $\mu$m was coated with the following composition:

| | |
|---|---|
| methylene chloride | 9.5 ml |
| methanol | 0.5 ml |
| ESTANE 5715 (ESTANE is a registered trade mark of the B. F. Goodrich Chem. Co. for a polyurethane resin | 0.5 g |
| triphenyl phosphate | 0.25 g |
| 2,2',6,6'-tetramethyl-4,4'-dihydroxydiphenyl (as dye precursor) | 0.054 g |
| photo-oxidant of Table 1 | 2.276 × $10^{-4}$ mole | at a wet coating thickness of 50 $\mu$m.

After drying at 40° C. in a ventilated stove the obtained photosensitive recording materials were exposed with a HANAU Q 400 high pressure mercury vapour lamp (HANAU is a registered trade mark).

The radiation of said lamp was filtered to have transmitted only radiation in the wavelength region of 240 to 400 nm.

In Table 1 the amount of photo-oxidants in the coating composition is given together with the relative exposure times necessary to obtain an optical density of 1,00. The optical density was measured with a MACBETH (registered trade mark) Quantalog TD 102 densitometer equipped with a blue filter. The exposure time of Example 1 was given arbitrarily the value 1.

TABLE 1

| Example | photo-oxidant | amount in g | relative exposure time |
|---|---|---|---|
| 1 | dimer A | 0.122 | 1 |
| 2 | trimer A | 0.183 | 4 |
| 3 | dimer B | 0.122 | more than 100 |

EXAMPLES 4-9

These examples relate to comparable photosensitive recording materials containing a different photopolymerizable layer suited for use in the production of a photoresist on an etchable metal layer.

A polyethylene terephthalate support of a thickness of 100 μm carrying a vacuum-deposited bismuth layer of 0.15 μm was coated consecutively with the two following compositions.

First layer composition

| pentaerythritol tetraacrylate | 10.25 g |
|---|---|
| 2-mercapto-benzoxazole | 0.05 g |
| photo-oxidant of Table 2 | $1.42 \times 10^{-3}$ mole |
| methylene chloride | 60 ml |

The layer was applied at a wet coating coverage of 25 g per sq.m and dried at 25° C. with an air current.

Second layer composition

| polyvinyl alcohol | 5 g |
|---|---|
| TRITON X 100 (TRITON is a registered trade mark of Rohm & Hass Co. for an octylphenoxy polyethoxyethanol dispersing agent) | 1 ml |
| water to make | 100 ml |

The layer serving as oxygen barrier was applied as a wet coating coverage of 50 g per sq.m and dried at 45° C. with an air current.

Exposure and processing

The photosensitive recording materials were exposed in contact with a halftone transparency with a light source as defined in Table 2.

After the exposure the outer layer (second layer) was removed by washing for 1 min with tap water at 37° C. Subsequently the unexposed parts of the first layer were removed by treatment with methanol at 20° C. for 1 min.

After drying, each photosensitive recording material was dipped into a 37% aqueous solution of iron(III) chloride therewith removing the bare bismuth portions.

After washing with tap water and drying, the photosensitive recording materials contain black bismuth metal parts covered with polymerized coating corresponding with the radiation-transmitting parts of the original.

In Table 2 the relative sensitivity is expressed as the inverse of the exposure time necessary to obtain the image result of the photosensitive recording material of Example 4, the exposure time of which is given arbitrarily the value 1.

TABLE 2

| Example | photo-oxidant | amount | radiation unit | relative sensitiity |
|---|---|---|---|---|
| 4 | dimer A | 0.76 g | I | 1 |
| 5 | BI | 0.94 g | I | 0.70 |
| 6 | dimer A | 0.76 g | II | 0.28 |
| 7 | BI | 0.94 g | II | 0.28 |
| 8 | dimer A | 0.76 g | III | 0.65 |
| 9 | BI | 0.94 g | III | 0.65 |

BI = bis(2-o-chlorophenyl-4,5-diphenyl/imidazolyl)
I = CHEMCUT (registered trademark of Chemcut Corporation) exposure apparatus equipped with 6 20 W Philips TL 20 W08 fluorescent tubes having a peak output at 350 nm
II = Xenon lamp OSRAM (registered trademark) XBO 1000 W/HS equipped with BALZERS (registered trademark) Filter R-UV 312.20
III = HANAU (registered trademark) Q 400 equipped with BALZERS (registered trademark) Filter R-UV 312.20.

From the results in Table 2 may be concluded that for ultraviolet radiation of 350 nm the sensitivity of dimer A is higher than of the mentioned prior art BI-compound.

EXAMPLES 10-11

The photosensitive recording materials A and B of these examples contain a heterogeneous photopolymerizable layer including an addition-polymerizable monomer dispersed in a hydrophilic colloid binder. In material A Michler's ketone is present as spectral sensitizing agent.

A polyethylene terephthalate support of a thickness of 100 um carrying a vacuum-deposited bismuth layer of 0.15 μm was coated with one of the following compositions A or B listed in Table 3.

TABLE 3

|  | Comp. A | Comp. B |
|---|---|---|
| pentaerythritol tetraacrylate | 2.05 g | id. |
| dimer A | 0.61 g | id. |
| 2-mercaptobenzoxazole | 0.04 g | id. |
| Michler's ketone | 0.02 g | none |
| gelatin | 2.5 g | id. |
| 10% aqueous solution of lauryl benzene sulphonic acid sodium salt | 0.7 ml | id. |
| water to make | 50 g | id. |

In the preparation of the coating compositions of materials A and B the first four ingredients of composition A and the first three ingredients of composition B were dissolved in 8 ml of methylene chloride and added respectively to their last three ingredients in a homogenizer to form an emulsion by high-speed stirring. In the emulsification step the temperature of the emulsions was kept at 35° C. by water bath cooling. Thereupon the methylene chloride was removed from the emulsion in a rotary evaporator operating under reduced pressure with a water pump and heated on a water bath at 45° C.

The evaporation was continued till an emulsion portion of 45 g was left whereto water was added to make 50 g. The coating of both emulsions A and B was effected at a wet coverage of 25 g per sq.m. The coated layers were gelled at room temperature for 1 min and dried in a ventilated stove at 50° C.

The materials A and B were exposed through a step wedge having an increment of 0.15.

In the exposure of these materials A and B radiation source I of Table 2 (see Examples 4–9) was used. The exposure time was 5 s and proceeded through a grey filter having the density 1.00.

A RAPILITH Etch RE 410 apparatus (RAPILITH is a registered trade mark of Agfa-Gevaert N.V. Belgium) was used for processing, the first tray thereof containing a 34% aqueous iron(III) chloride solution and the second tray tap water at room temperature. The transport speed was set at 0.5 cm.s$^{-1}$.

In both materials A and B a negative copy of the original was obtained.

In Table 4 the relative radiation sensitivity of material A was given arbitrarily the value 1.

TABLE 4

| Example | material | spectral sensitizer | relative sensitivity |
|---------|----------|---------------------|----------------------|
| 10 | A | Michler's ketone | 1 |
| 11 | B | none | 0.46 |

EXAMPLE 12

This example illustrates the insufficient stability of bis(2,4,5-triphenylimidazolyl), also called dilophine, in the heterogeneous photopolymerizable composition of Example 11.

In said composition dimer A is replaced by 0.67 g of dilophine.

After coating, drying and applying the exposure and processing conditions of Example 11 no image-wise etching of the bismuth layer was possible, which leads to the conclusion that in the emulsification step polymerization started and proceeded already up to a degree wherein it was no longer possible to obtain image differentiation by the described photo-exposure.

EXAMPLES 13–14

These examples illustrate the better thermal stability of present dimer A as compared to dilophine in a print-out image dye-forming composition.

As described in Examples 1–3 two photosensitive recording materials were prepared wherein, however, the photo-oxidants were dimer A and dilophine respectively.

In table 5 the amounts of photo-oxidants used are given together with optical density results obtained after storage (1) in the dark at 60° C. for 2 h and (2) at 22° C. for 4 days. The optical densities were measured as described in Examples 1–3.

TABLE 5

| | | | optical density | |
|---|---|---|---|---|
| Example | photo-oxidant | amount in g | fresh | 2h at 60° C. | 4d at 22° C. |
| 13 | dimer A | 0.122 | 0.06 | 0.06 | 0.06 |
| 14 | dilophine | 0.134 | 0.06 | 1.38 | 0.40 |

From these optical density values obtained by thermal treatment (60° C.) and storage at room temperature (22° C.) in the dark it is clear that dilophine is too thermosensitive for practical use in a print-out photographic material.

EXAMPLE 15

This example illustrates the use of the emulsion layer of material A described in Example 10 in a wash-off imaging processing for the production of a relief image.

The emulsion A was coated onto a subbed polyethylene terephthalate film at a wet coverage of 25 g per sq.m.

After gelling and drying as described in Examples 10–11, the material was contact-exposed through a step wedge (increment 0.15) for 60 s in a SPEKTRA-PROOF (registered trade mark of Siegfried Theimer GmbH, 6484 Birstein-W. Germany) apparatus equipped with a high-pressure mercury vapour lamp of 2000 Watt doped with iron(III) chloride and operating at half power.

The exposed material was developed by washing with water of 37° C. for 1 min. The material was then soaked in a concentrated aqueous solution of methylene blue for 1 min, briefly washed with tap water and dried.

A blue negative relief print of the original was obtained showing a full coloured area corresponding with five steps of the original step wedge.

EXAMPLE 16

Example 1 was repeated with the difference however, that 0.122 g of the product, obtained by said washing technique (see preparation A) were used instead of the column chromatography-purified product. The photographic sensitivity of the material was substantially the same as that of Example 1.

We claim:

1. A photosensitive recording material comprising a supported or self-supporting binder layer incorporating an organic photoradical precursor compound in operative relationship with an image-forming precursor compound which is capable of taking part in image formation by reaction with photoradicals formed by photoexposing said photoradical precursor compound, characterized in that (1) the photoradical precursor compound is a di- or tri(2,3-aryl substituted indolyl) compound free from Zerewitinoff active hydrogen, and is within the scope of the following general formulae:

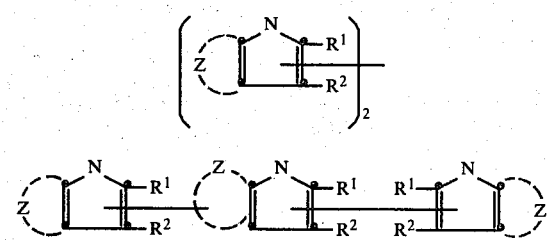

wherein:

Z represents the atoms necessary to close an adjacent carbocyclic aromatic ring, and each of $R^1$ and $R^2$ is an aryl substituent or a substituted aryl substituent, the positions of the double bonds in the indole rings being determined by the position of the linkage between the rings, and (2) the image-forming precursor compound is selected from the group consisting of (a) a reducing compound containing Zerewitinoff active hydrogen and (b) a free radical polymerizable non-gaseous ethylenically unsaturated compound in combination with a free radical producing electron-donor agent.

2. Photosensitive material according to claim 1, characterized in that each of $R^1$ and $R^2$ represents a phenyl group.

3. Photosensitive material according to claim 1, characterized in that said image-forming precursor compound is a reducing compound forming a coloured compound by reaction with the photoradicals released upon exposure of said indolyl compound.

4. Photosensitive material according to claim 1, characterized in that said image-forming precursor compound is a leuco dye adapted to undergo oxidation with free radicals formed by ultraviolet irradiation of said indolyl compound, and said material also contains a redox couple capable of producing by exposure to visible light a reductant scavenging indolyl radicals formed in a subsequent ultraviolet exposure of the material to form colourless products.

5. Photosensitive material according to claim 1, characterized in that the indolyl compound is present in a binder layer on a support in operative relationship with
   (1) at least one non-gaseous ethylenically unsaturated compound capable of free-radical-initiated, chain-propagating addition polymerization, and
   (2) a free radical producing electron-donor agent from which an electron can be abstracted by a photolytically formed indolyl radical of said indolyl compound to yield a free radical which reacts with the unsaturated compound (1) to initiate the addition polymerization thereof.

6. Photosensitive material according to claim 1, characterized in that the material contains a photopolymerizable layer including hydrophilic binder having uniformly dispersed therethrough a dispersed phase containing
   (1) at least one water-insoluble ethylenically unsaturated monomer capable of forming a polymer by free-radical-initiated chain-propagating addition polymerization, and
   (2) at least one composition producing free radicals and activatable by ultraviolet radiation to yield free-radical polymerization photoinitiator(s), said composition containing said indolyl compound and at least one free radical producing electron-donor agent from which an electron can be abstracted by a photolytically formed indolyl radical of said indolyl compound.

7. Photographic material according to claim 6, characterized in that the photopolymerizable layer is applied to a supported etchable metal layer.

* * * * *